(12) United States Patent
Cohen et al.

(10) Patent No.: US 12,133,689 B2
(45) Date of Patent: Nov. 5, 2024

(54) DISPLAYING ANNOTATIONS ON DESIGN LINE FORMED ON ANATOMICAL MAP

(71) Applicant: BIOSENSE WEBSTER (ISRAEL) LTD., Yokneam (IL)

(72) Inventors: Assaf Cohen, Kiryat Bialik (IL); Fady Massarwa, Baka Al Gharbiyya (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 988 days.

(21) Appl. No.: 17/129,995

(22) Filed: Dec. 22, 2020

(65) Prior Publication Data
US 2022/0192748 A1 Jun. 23, 2022

(51) Int. Cl.
*A61B 34/10* (2016.01)

(52) U.S. Cl.
CPC ........ *A61B 34/10* (2016.02); *A61B 2034/105* (2016.02); *A61B 2034/107* (2016.02)

(58) Field of Classification Search
CPC .................................................... A61B 34/10
USPC ....................................................... 600/508
See application file for complete search history.

(56) References Cited

U.S. PATENT DOCUMENTS

| | | |
|---|---|---|
| 5,391,199 A | 2/1995 | Ben Haim |
| 6,239,724 B1 | 5/2001 | Doron |
| 6,332,089 B1 | 12/2001 | Acker |
| 6,484,118 B1 | 11/2002 | Govari |
| 6,618,612 B1 | 9/2003 | Acker |
| 6,690,963 B2 | 2/2004 | Ben Haim |
| 2002/0065455 A1 | 5/2002 | Ben Haim |
| 2003/0120150 A1 | 6/2003 | Govari |
| 2004/0068178 A1 | 4/2004 | Govari |
| 2011/0230775 A1 | 9/2011 | Barley |
| 2013/0006131 A1* | 1/2013 | Narayan ............. A61B 5/4029 606/32 |
| 2014/0142422 A1 | 5/2014 | Manzke |

FOREIGN PATENT DOCUMENTS

| | | |
|---|---|---|
| EP | 3335657 A1 | 6/2018 |
| WO | WO1996005768 A1 | 2/1996 |
| WO | WO2017160808 A1 | 9/2017 |

OTHER PUBLICATIONS

European Search Report for corresponding EPA No. 21216437.0 dated Jun. 10, 2022.

* cited by examiner

*Primary Examiner* — Nadia A Mahmood
(74) *Attorney, Agent, or Firm* — Gabriel Azar

(57) ABSTRACT

A method, includes receiving an anatomical map of a patient organ, the anatomical map including properties obtained at respective locations on a first surface of the organ. A design line produced on a second surface of the anatomical map, is received. One or more of the properties that, when falling along the design line, will be visualized thereon, are selected, and the one or more properties falling along the design line, are visualized.

20 Claims, 3 Drawing Sheets

DISPLAYING ANNOTATIONS ON DESIGN LINE FORMED ON ANATOMICAL MAP

FIELD OF THE INVENTION

The present invention relates generally to medical devices, and particularly to methods and systems for displaying annotations on a design line of an anatomical map.

BACKGROUND OF THE INVENTION

Various techniques for displaying information on anatomical images have been published.

For example, U.S. Pat. No. 9,891,784 describes a method of displaying a medical image. The method includes displaying a first image that is generated by rendering volume data of an object in a first direction, displaying on the first image a viewer tool for generating a second image, wherein the viewer tool indicates a section of the object, generating the second image by rendering sub-volume data included in the volume data in a second direction which is different from the first direction and indicated by the viewer tool, and displaying at least a part of the second image.

U.S. Pat. No. 10,489,907 describes a medical scanner that generates a medical image that may have an artifact. A machine-learnt detector, trained from a library of many different types of artifacts in images, detects any artifact in the medical image for a patient. The location of the artifact is highlighted, providing an indication of possible artifact where the image may otherwise appear to represent anatomy or pathology. A machine-learnt network may be applied to the medical image to determine a correction, such as different scan or reconstruction, to remove or reduce the artifact.

SUMMARY OF THE INVENTION

An embodiment of the present invention that is described herein provides a method, including receiving an anatomical map of a patient organ, the anatomical map including properties obtained at respective locations on a first surface of the organ. A design line produced on a second surface of the anatomical map, is received. One or more of the properties that, when falling along the design line, will be visualized thereon, are selected. The one or more properties falling along the design line, are visualized.

In some embodiments, the second surface models the first surface in the anatomical map. In other embodiments, the design line is selected from a list of design lines consisting of: (i) a linear path, (ii) a circular path, and (iii) a path having a bifurcation shape. In yet other embodiments, receiving the design line includes receiving a planning of one or more ablation lines for ablating tissue on the first surface of the organ.

In an embodiment, the organ includes a heart, and selecting the properties include selecting at least one of the one or more properties from a list of properties consisting of: (i) a local activation time of a wave propagating in the heart, (ii) a local direction of the wave propagating in the heart, (iii) a fractionated electrical signal, (iv) a conduction speed of the wave propagating in the heart, (v) an electrical parameter of an electrical signal in the heart, (vi) a scar in tissue of the heart, and (vii) an intersection of waves propagating in the heart. In another embodiment, visualizing the properties includes applying, to the design line, one or more types of annotations indicative of a respective property of the one or more properties. In yet another embodiment, at least one of the annotations is selected from a list of annotations consisting of: (i) a jagged section of the design line, (ii) an altering thickness of a first respective section of the design line, (iii) an altering color of a second respective section of the design line, (iv) a geometric shape marked on a third respective section of the design line, and (v) first and second geometrical shapes placed, respectively, at first and second locations on the design line, so as to form a given section having the respective property.

In some embodiments, at least one of the altering thickness and altering color is indicative of a magnitude of the respective property. In other embodiments, the first and second geometrical shapes include first and second lines orthogonal to the design line, and the respective property includes a scar contained within the given section. In yet other embodiment, the method further including, in response to visualizing the one or more properties falling along the design line, adjusting at least one of: (i) a path of the received design line, and (ii) the selection of at least one of the properties.

There is additionally provided, in accordance with an embodiment of the present invention, a system including a processor and an output device. The processor is configured to: (i) receive an anatomical map of a patient organ, the anatomical map including properties obtained at respective locations on a first surface of the organ, (ii) receive a design line produced on a second surface of the anatomical map, and select, or receive a selection of, one or more of the properties that, when falling along the design line, will be visualized thereon. The output device is configured to visualize the one or more properties falling along the design line.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Figure 1:
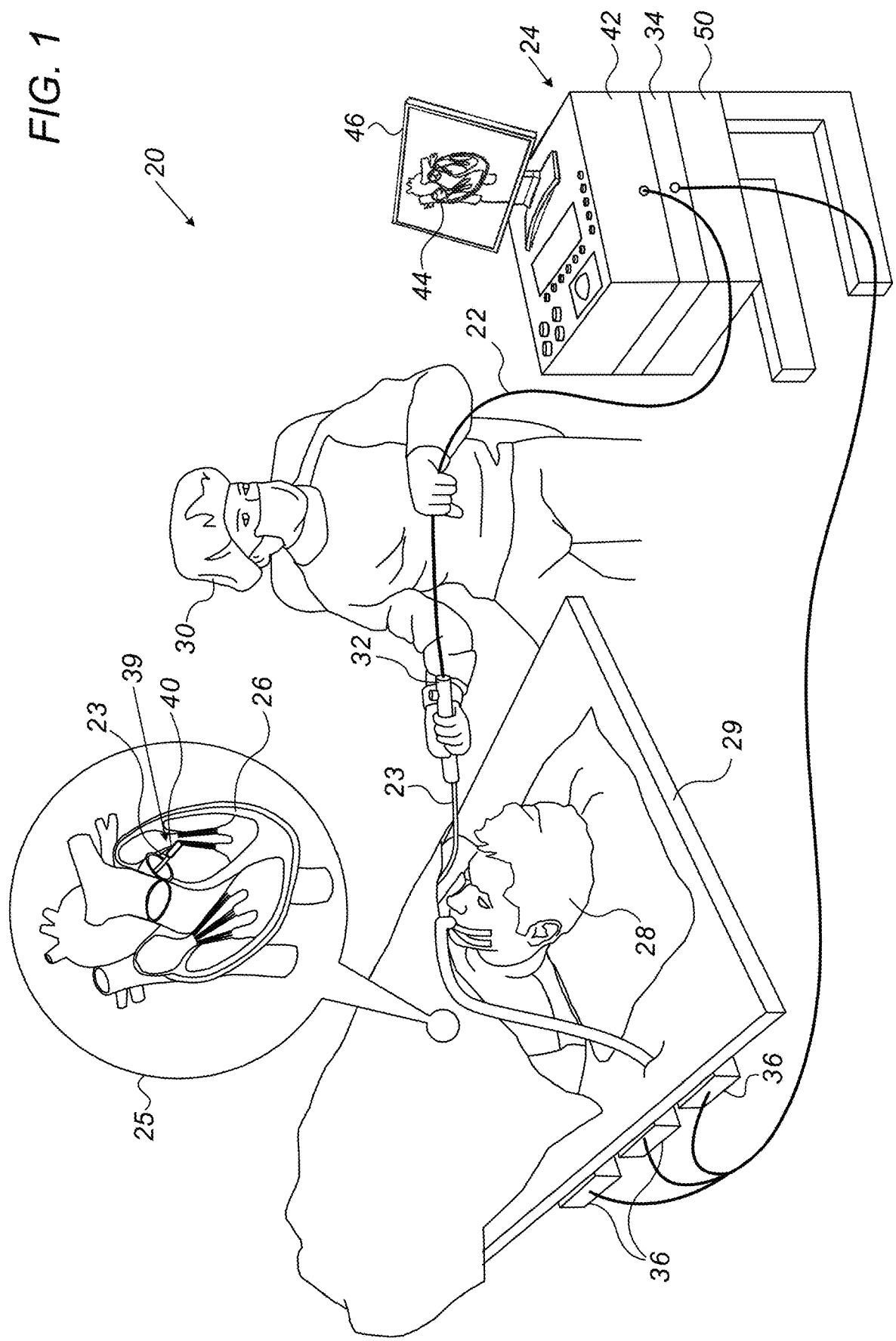
FIG. 1 is a schematic, pictorial illustration of a catheter-based position-tracking and ablation system, in accordance with an exemplary embodiment of the present invention.

Some medical procedures, such as radiofrequency (RF) ablation of heart tissue, are planned by measuring various properties at one or more regions of interest (ROIs) of the heart, and based on the measured properties, drawing a design line on the surface of an anatomical map of the heart.

The measured properties are typically obtained by moving a mapping probe across selected areas of the heart, e.g., for acquiring electro-anatomical signals, and based on the acquired signals, displaying one or more spatial distributions of the measured properties. When a physician uses a design line tool for producing a design line (e.g., by marking an ablation line) on the surface of the anatomical map, he/she has to review different maps of showing two-dimensional (2D) maps of different properties, and in some cases merge some maps together, so as to determine an accurate path of the ablation line. This methodology is time consuming and may result in mistakes made by the physician, inter alia, due to a comparison between different 2D anatomical maps showing different properties at similar or different areas on the heart surface.

Embodiments of the present invention that are described hereinbelow provide improved techniques for displaying annotations on a design line produced on the surface of an anatomical map of the patient organ. In the present example, the organ comprises a heart, the design line comprises planning of an ablation line, and the annotations are indicative of properties of the heart falling along the ablation line.

In some embodiments, a system for displaying the annotations comprises a processor and an output device, such as a display. The processor is configured to receive an anatomical map of the patient heart. The anatomical map comprising properties obtained (e.g., measured) at respective locations on the surface of the heart. The processor is further configured to receive, typically from a physician that plans the ablation procedure, a planned ablation line (or any other suitable type of a design line) produced on the surface of the anatomical map.

In some embodiments, the physician may select one or more of the properties that, when falling along the design line, will be visualized thereon. The properties may be selected manually by the physician, or automatically by the processor, or using any suitable combination thereof, e.g., properties recommended by the processor and approved or adjusted by the physician.

In some embodiments, the processor is configured to visualize the one or more properties falling along the ablation line, using any suitable type of annotations, and the display is configured to display the annotations on the ablation line of the anatomical map.

In some embodiments, the ablation line may comprise a linear path, for example, in case of a linear ablation along a surface of the heart. In other embodiments, the ablation line may comprise a circular path, for example, in a pulmonary vein isolation procedure, in which the ablation line forms a perimeter surrounding one or more veins of an atria of the heart. In alternative embodiments, the design line may have a bifurcation shape, for example, when two waves collide and merge into a single wave. Note that in the disclosed techniques, the properties are displayed along a line (e.g., the ablation line), rather than across areas of the anatomical map.

In some embodiments, the properties may be selected from a list of properties of the heart, which are measured and/or calculated based on the measurements. The list may consist, for example: (i) a local activation time (LAT) of a wave propagating in the heart, (ii) a local direction of the wave propagating in the heart, (iii) a fractionated electrical signal, (iv) a conduction speed of the wave propagating in the heart, (v) a voltage, or any other electrical parameter of a unipolar or bipolar signal measured in the heart, and (vi) a scar in tissue of the heart (where the measured voltage is about zero because signals are not propagating across the scar), and (vii) an intersection or collision of two or more waves propagating in the heart.

In some embodiments, the properties may be displayed on the surface of the anatomical map using any suitable type of annotations. For example, (i) the LAT may be displayed using color coding or one or more numbers, (ii) the local direction of the wave propagating in the heart may be annotated using an arrow indicative of the direction of propagation, (iii) the fractionated electrical signal may be annotated using a jagged line, (iv) the conduction speed of the wave propagating may be annotated using an altering thickness of the ablation line, e.g., a thick ablation line may be indicative of slow speed, (v) the voltage of the unipolar or bipolar signal may be annotated using color coding, and (vi) the scar may be annotated using two short lines, which are orthogonal to the ablation line and are positioned at the ends of the scar, and (vii) the collision of two or more waves propagating in the heart, may be annotated using an "X" marker.

In some embodiments, the processor is configured to calculate an ablation index along the ablation line. The ablation index comprises a combination of parameters related to the amount of ablation required at a respective position along the ablation line. For example, the ablation index may be indicative of a combination of at least the following parameters required for the ablation: (i) contact force applied between the ablation electrode and the tissue at the ablation site, (ii) the ablation energy applied to the tissue, and (iii) the duration of the ablation at the respective point along the ablation line.

In some embodiments, the annotation of the ablation index may comprise a circle overlaid on the ablation line, wherein the diameter of the circle is indicative of the calculated size of the ablation index. For example, a large diameter is indicative of a large ablation index.

The disclosed techniques may be used for displaying, along a one-dimensional design line, multiple parameters and properties, which are typically presented using multiple 2D maps, wherein each map displays spatial distribution of a different parameter. Therefore, visualizing multiple properties and parameters along the design line assists the physician in the planning of the ablation procedure.

Therefore, the disclosed techniques improve the quality of ablation procedures, by (i) providing the physician with annotations displayed automatically and dynamically along a planned ablation line, (ii) reducing the time for planning the ablation procedure, and (iii) reducing potential errors in the definition of the ablation line.

System Description

FIG. 1 is a schematic, pictorial illustration of a catheter-based position-tracking and ablation system 20, in accordance with an embodiment of the present invention. In some embodiments, system 20 comprises a catheter 22, in the present example a cardiac catheter, and a control console 24. In the embodiment described herein, catheter may be used for any suitable therapeutic and/or diagnostic purposes, such as ablation of tissue in a heart 26 and/or for mapping cardiac arrhythmias by sensing intra-cardiac electrical signals.

In some embodiments, console 24 comprises a processor 42, typically a general-purpose computer, with suitable front end and interface circuits for exchanging signals with catheter 22 (e.g., receiving intra-cardiac electrical signals and applying ablation pulses to tissue of heart 26), and for controlling other components of system 20 described herein. Processor 42 may be programmed in software to carry out the functions that are used by the system, and is configured to store data for the software in a memory 50. The software may be downloaded to console 24 in electronic form, over a network, for example, or it may be provided on non-transitory tangible media, such as optical, magnetic or electronic memory media. Alternatively, some or all of the functions of processor may be carried out using an application-specific integrated circuit (ASIC) or any suitable type of programmable digital hardware components.

Reference is now made to an inset 25. In some embodiments, catheter 22 comprises a distal-end assembly 40, and a shaft 23 for inserting distal-end assembly 40 to a target location for ablating tissue in heart 26. During an ablation procedure, physician 30 inserts catheter 22 through the vasculature system of a patient 28 lying on a table 29. Physician 30 moves distal-end assembly 40 to the target location in heart 26 using a manipulator 32 near a proximal end of catheter 22, which is connected to interface circuitry of processor 42.

In some embodiments, catheter 22 comprises a position sensor 39 of a position tracking system, which is coupled to the distal end of catheter 22, e.g., in close proximity to distal-end assembly 40. In the present example, position sensor 39 comprises a magnetic position sensor, but in other embodiments, any other suitable type of position sensor (e.g., other than magnetic-based) may be used.

Reference is now made back to the general view of FIG. 1. In some embodiments, during the navigation of distal-end assembly 40 in heart 26, processor 42 receives signals from magnetic position sensor 39 in response to magnetic fields from external field generators 36, for example, for the purpose of measuring the position of distal-end assembly 40 in heart 26. In some embodiments, console 24 comprises a driver circuit 34, configured to drive magnetic field generators 36. Magnetic field generators 36 are placed at known positions external to patient 28, e.g., below table 29.

In some embodiments, processor 42 is configured to display, e.g., on a display 46 of console 24 or on any other suitable output device, the tracked position of distal-end assembly 40 overlaid on an image 44 of heart 26. In some embodiments, processor 42 is configured to display an anatomical map (shown in FIG. 2 below) of at least part of heart 26.

The method of position sensing using external magnetic fields is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publication Nos. 2002/0065455 A1, 2003/0120150 A1 and 2004/0068178 A1, whose disclosures are all incorporated herein by reference.

This particular configuration of system 20 is shown by way of example, in order to illustrate certain problems that are addressed by embodiments of the present invention and to demonstrate the application of these embodiments in enhancing the performance of such a system. Embodiments of the present invention, however, are by no means limited to this specific sort of example system, and the principles described herein may similarly be applied to other sorts of medical systems.

Displaying Annotations on Design Line Formed on Anatomical Map

Figure 2:
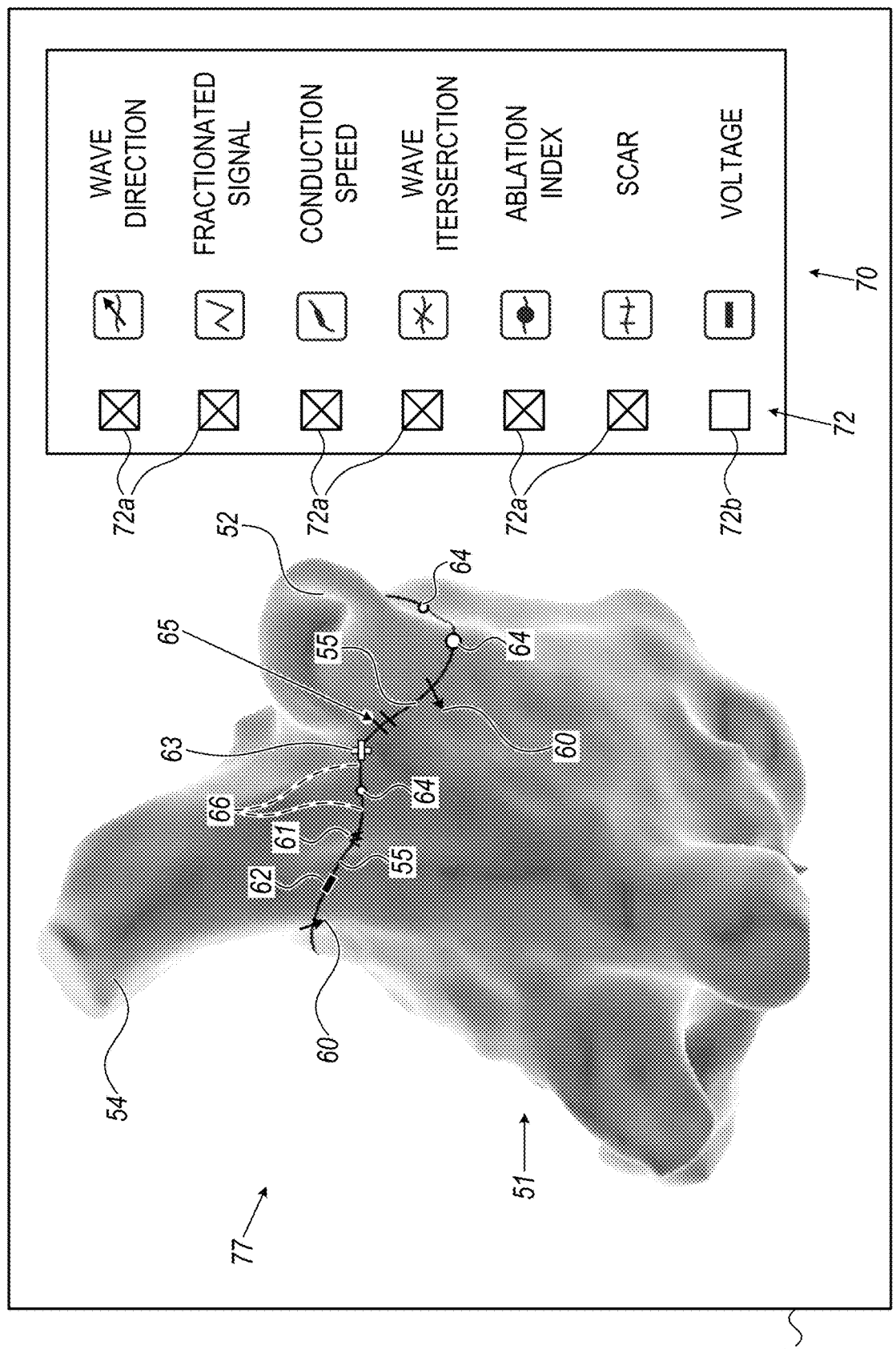
FIG. 2 is a schematic, pictorial illustration of annotations displayed on a design line of a left atria, in accordance with an exemplary embodiment of the present invention.

FIG. 2 is a schematic, pictorial illustration of annotations displayed on a design line 55 formed on an anatomical map 77 of heart 26, in accordance with an embodiment of the present invention.

In some embodiments, processor 42 displays on an output device, such as display 46, the anatomical map of a left atria 51 of heart 26. In the present example, display 46 displays anatomical map 77 solely with the geometrical features of the anatomy of left atria 51, but in other embodiments, processor 42 is configured to display on anatomical map 77 any suitable properties of left atria 51. For example, local activation time of waves propagating in heart 26, conduction speed of the waves, unipolar or bipolar voltage measured at respective positions of heart 26, and other properties described in detail below. Note that such properties may be displayed using color coding of areas within left atria 51, which are indicative of the amplitude of the respective property, or using any suitable type of annotations. For example, red and blue colors may be indicative of high (e.g., about 4 V) and low (e.g., about 0.1 mV) bipolar voltages measured, for example, between two electrodes of distal-end assembly 40 at respective positions of left atria 51.

In the present example, the ablation procedure comprises pulmonary vein (PV) isolation of veins 52 and 54 of left atria 51 for treating arrhythmia in heart 26. In some embodiments, physician 30 controls processor 42 to display left atria 51 on image 44, and uses any suitable input devices of console 24 to form a design line 55 surrounding veins 52 and 54 of left atria 51. In the present example, the design line comprises an ablation line for performing the PV isolation by ablating the tissue along the ablation line. Note the physician 30 is drawing the ablation line based on clinical considerations, which are derived, inter alia, from the aforementioned properties of left atria 51.

In principle, when physician 30 produces design line 55 on the surface of the anatomical map 77, he/she has to review different maps of different respective properties, so as to determine an accurate path of design line 55, which is the ablation line in this case. This methodology is time consuming and may result in mistakes made by physician 30. Such mistakes may be caused, for example, due to a comparison between different 2D anatomical maps that show spatial distributions of multiple properties measured and/or displayed at similar or different areas on the surface of heart 26. Moreover, processor 42 is configured to overlay on anatomical map 77, multiple maps of corresponding properties consolidated or merged and displayed on anatomical map 77. However, a congestion of properties displayed spatially across areas of the anatomical map of left atria 51 may confuse physician 30 and may interfere with the clinical considerations used for determining the path of design line 55.

In some embodiments, during the mapping of left atria 51, processor 42 is configured to receive from distal-end assembly 40, measurements performed when physician 30 moves catheter 22 along selected areas (or all areas) of left atria 51. Processor 42 is configured to derive from the measurements, one or more anatomical and electro-anatomical properties of left atria 51. For example, processor 42 is configured to calculate waves propagating in tissue of left atria 51, and display the local activation time (LAT) of the wave at respective positions of left atria 51. For example, processor 42 may assign a purple color to a starting point of a given wave, and a red color to an ending point of the given wave. Processor 42 is further configured to calculate and display the propagation the direction and propagation speed of the given wave, and a point of intersection or collision between two waves crossing one another when propagating in left atria 51.

In some embodiments, processor 42 is configured to display the voltage amplitude measured at respective positions on left atria 51. The measurements may be performed using a unipolar configuration (e.g., between an electrode of distal-end assembly 40 and a patch electrode (not shown) coupled to the skin of patient 28) or a bipolar configuration (e.g., between two electrodes of distal-end assembly 40).

In some cases, an electrocardiogram (ECG) signal received from the electrode(s) of distal-end assembly 40 may be fractionated. In some embodiments, processor 42 is configured to identify such fractionated signals and to associate them with respective positions on the tissue of left atria 51. Similarly, processor 42 is configured to identify one or more scars that occur in left atria 51, e.g., based on the measured voltage (typically zero) and other indications, such as deviation in the propagation direction of the wave in left atria 51.

In some embodiments, processor 42 is configured to calculate an ablation index at a respective position on the surface of anatomical map 77. In the context of the present disclosure and in the claims, the term "ablation index" refers to a metric indicative of the ablation required to be performed at the respective position. In other words, the ablation index comprises a combination of parameters related to the amount of ablation required at the respective position. For example, the ablation index may be indicative of a combination of at least the following parameters required for the ablation: (i) contact force applied between the ablation electrode and the tissue at the ablation site, (ii) the ablation energy applied to the tissue, and (iii) the duration of the ablation at the respective point.

In some embodiments, one or more of the properties that, when falling along design line 55, are selected to be visualized at the suitable positions along design line 55. The properties may be selected manually by physician 30, or automatically by processor 42, or using any suitable combination thereof, e.g., properties recommended by processor 42 and approved or adjusted by physician 30.

In some embodiments, processor 42 is configured to display, on display 46, a legend 70 comprising a list of at least the properties described above, and selection boxes 72 indicative whether each of the respective parameters has been selected. As will be described in detail below, processor 42 is configured to visualize one or more (typically multiple) selected properties that fall on design line 55. In such embodiments, processor 42 is configured to display, along (a one-dimensional) design line 55, multiple parameters and properties, which are typically presented using multiple 2D maps, each map displays spatial distribution of a different parameter. Presenting multiple properties and parameters along design line 55 assists physician 30 in the planning of the ablation procedure.

In some embodiments, processor 42 is configured to assign annotations for visualizing the selected parameters in legend 70, and to display the properties falling on respective positions along design line 55. In the present example, legend 70 comprises the following visualizations and/or annotations of properties: (i) an annotation 60 comprises an arrow indicative of the direction of a wave propagating along left atria 51 and coming across design line 55, (ii) an annotation 61 comprises a jagged line indicative of a fractionated ECG signal obtained at one or more respective section(s) of design line 55, (iii) an alteration of the thickness of design line 55, indicative of the conduction speed of the wave at a respective position of left atria 51 falling on a respective section of design line 55. In the present example, an annotation 62 comprises a thicker line on design line 55 is indicative of a slower speed (e.g., about 1 mm/msec relative to an average propagation speed of about 5 mm/msec) of the respective wave propagating along left atria 51.

In some embodiments, processor 42 is configured to assign additional annotations for visualizing the selected parameters in legend 70, for example, processor 42 is configured to assign an annotation 63 having an X-shape, which is overlaid on design line 55 and is indicative of a collision or intersection described above between waves propagating across left atria 51, wherein the waves are colliding along a respective section of design line 55. In some cases the intersection may be between two LATs of the same wave, also refers to herein as "early meets late" with an early activation time meets a later activation time of the same wave, for example, due to a barrier that affects the propagation of the wave across left atria 51 of heart 26.

In some embodiments, processor 42 is configured to assign one or more circular annotations 64, also referred to herein as circles, overlaid on design line 55, wherein the diameter of the circle is indicative of the calculated size of the ablation index. For example, a large diameter (e.g., having a diameter of about 3 cm) is indicative of a large ablation index (e.g., about 200), and a small diameter (e.g., having a diameter of about 1 cm) is indicative of a smaller ablation index (e.g., about 400).

In some embodiments, processor 42 is configured to assign a sectional annotation 65, which is limited by two lines orthogonal to design line 55, for annotating a scar falling on design line 55. In an embodiment, annotation 65 may be indicative of a projection of the scar area on design line 55. In another embodiment, annotation 65 may be indicative of the physical part of the scar that falls on (e.g., coming across) design line 55.

In some embodiments, processor 42 is configured to assign to design line 55, a colored annotation 66 indicative of the voltage measured on tissue of left atria 51, at a respective section of design line 55. The color assignment depends on a range of the colors, For example, for a range between 0 and 100, red color is assigned to 0 and blue color is assigned to 100.

In the context of the present disclosure and in the claims, the terms "about" or "approximately" for any numerical values or ranges indicate a suitable dimensional tolerance that allows the part or collection of components to function for its intended purpose as described herein.

In the present example, selection boxes 72a of legend 70 are selected by physician 30 and/or by processor 42, whereas selection box 72b is not checked, and therefore, not selected. In such embodiments, processor 42 is configured to display annotations 60-65 that fall on design line 55 of anatomical map 77 of left atria 51, and not to display annotations 66 even though one or more of them are falling on design line 55. As shown in FIG. 2, processor 42 displays annotations 60-65 on respective sections of design line 55, and annotations 66, which, in the present example, are falling on two sections of design line 55, are not displayed. Note that the dashed lines connecting between numerals 66 and the respective sections, are not actually displayed in image 44 and are shown in FIG. 2 purely for the sake of presentation of the conceptual clarity. In some embodiments, in case selection box 72b will be selected, processor 42 will be displaying annotations 66 on the respective sections of design line 55.

In some embodiments, in the planning of the PV isolation procedure, physician 30 uses: (i) selection boxes for selecting annotations (and therefore, respective properties) to be displayed, and (ii) a design line tool (e.g., implemented in software in processor 42) for drawing design line 55, which is an ablation line planned to ablate tissue of left atria 51 for performing the PV isolation.

In some embodiments, processor 42 is configured to receive the selected annotations (e.g., annotations 60-65), and when physician 30 is drawing design line 55, processor is configured to display the selected annotations falling on corresponding sections along design line 55. Note that based on the displaying of such annotations, physician 30 may adjust the path of design line 55 so as to improve the ablation planning in left atria 51.

In other embodiments, processor 42 is configured to display the selected annotations only after physician 30 completes the drawing of design line 55.

The embodiments described in FIG. 2 are provided by way of example, and the present invention is not limited to what has been particularly shown and described in the example embodiments of FIG. 2. In other embodiments, processor 42 is configured to apply any other suitable type of annotations indicative of the same properties or any other properties measured and/or received and/or calculated for being annotated on design line 55 or on any other feature produced on any sort of anatomical map of heart 26 or any other organ of patient 28. Moreover, the embodiments described in FIG. 2 may be implemented using any other suitable techniques, instead of or in addition to the annotations and the design line described in FIG. 2.

Figure 3:
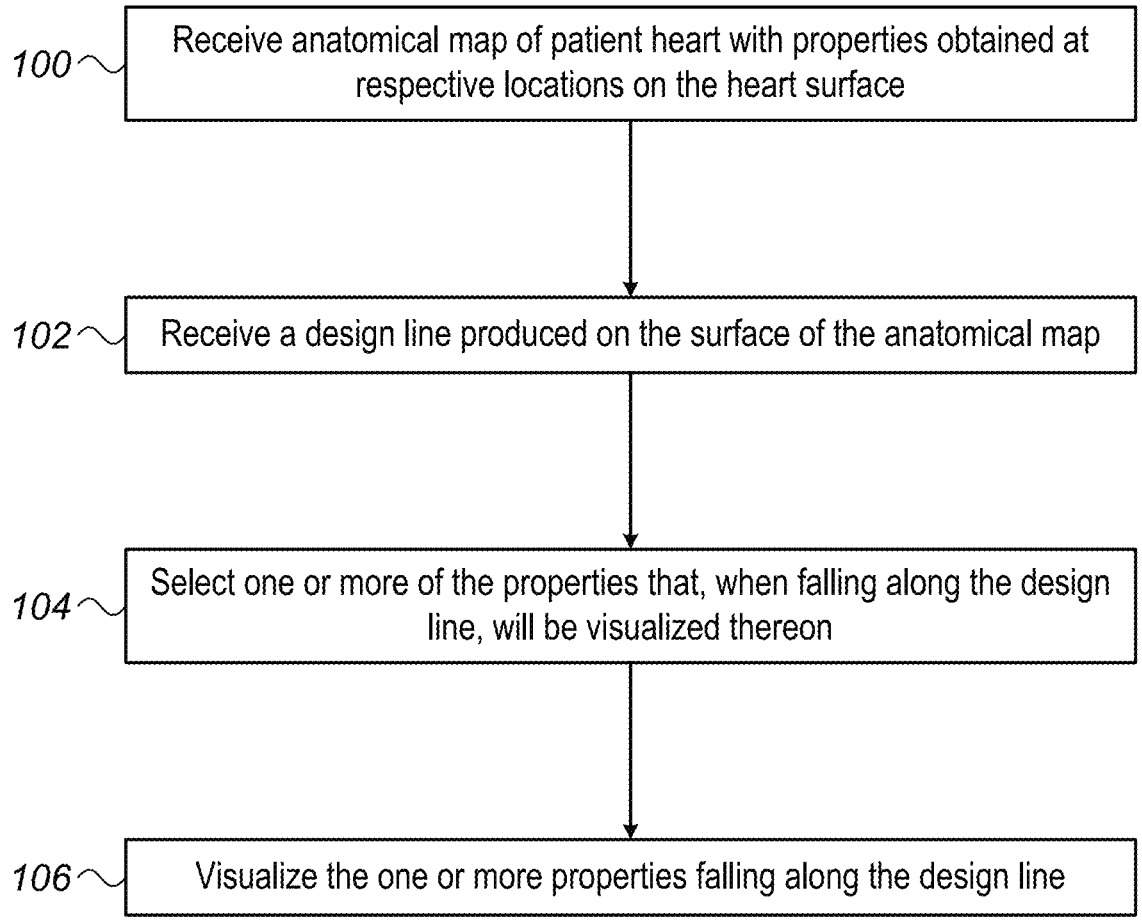
FIG. 3 is a flow chart that schematically illustrates a method for displaying annotations on a design line of an anatomical map, in accordance with an exemplary embodiment of the present invention.

FIG. 3 is a flow chart that schematically illustrates a method for displaying annotations 60-65 on design line 55 of anatomical map 77, in accordance with an embodiment of the present invention.

The method begins at an anatomical map receiving step 100 with processor 42 receiving anatomical map 77 of heart 26. In some embodiments, anatomical map 77 comprises properties obtained at respective locations on the surface of heart 26, as described in FIG. 2 above.

At a design line receiving step 102, processor 42 receives design line 55 produced by physician 30 (or any other user of system 20) on the surface of anatomical map 77. In the present example design line 55 comprises a circular line surrounding veins 52 and 54 of left atria 51, which is used for planning ablation along design line 55 so as to carry out the aforementioned PV isolation procedure, as described in FIG. 2 above. In other embodiments, processor 42 may receive any other sort of design line, which may be produced by physician 30 or imported from any suitable source. The design line may have a path having any suitable shape, such as but not limited to a circular shape (as shown in FIG. 3 above), a linear shape, a bifurcation shape (when two waves collide and merge into a single wave), or any other suitable shape and/or any other suitable type of design line, which is produced on the heart surface, along one or more produced or selected paths based on the clinical considerations of physician 30.

At a properties selection step 104, one or more of the properties described in FIG. 2 above, are selected. Note that, when falling along design line 55, the selected properties will be visualized on anatomical map 77. In the present example, the properties will be overlaid on corresponding sections of design line 55, as shown and described in detail in FIG. 2 above.

At a displaying step 106 that concludes the method, processor 42 displays on any suitable output device, such as display 46, a visualization of the one or more properties falling along the design line. In the present example, display 46 displays, in image 44, annotations 60-65 that fall at corresponding positions along design line 55. Note that, as described in detail in FIG. 2 above, the voltage measured along design line 55 were not selected (by physician 30 and/or processor 42), thus, annotations 66 (e.g., the colors indicative of the measured voltages) are not displayed in image 44.

In other embodiments, based on the displayed annotations, physician 30 may revise the path of design line 55, for example, in order to bypass one or more sections of the design line formed in step 102 above. In such embodiments, the method loops back to step 106 for adjusting the visualization of the annotations in response to the revised design line.

In yet other embodiments, after reviewing the visualization of step 106, physician 30 may adjust the selection of one or more of the properties. In the example of FIG. 2, physician 30 may check selection box 72b for displaying annotations 66 that fall on the revised path of design line 55. In such embodiments, processor 42 may repeat step 106 so as to include, in anatomical map 77, the visualization of annotations 66 that may fall on the revised path of design line 55.

Although the embodiments described herein mainly address visualization of properties on ablation lines, the methods and systems described herein can also be used in other applications, such as in treating atrial flutter. In this application, the user of system 20 (e.g., physician 30) can mark on the anatomical map: (i) a first design line indicative of the main circle, and (ii) a second design line indicative of the planned ablation line designed for breaking the main circle.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for displaying annotations on a design line provided on the surface of an anatomical map, comprising:
   receiving an anatomical map of a patient organ, the anatomical map comprising properties obtained at respective locations on a first surface of the organ;
   receiving a design line produced on a second surface of the anatomical map, wherein the second surface models the first surface in the anatomical map;
   selecting one or more of the properties that, when falling along the design line, will be visualized thereon; and
   visualizing the one or more properties falling along the design line.

2. The method according to claim 1, wherein the design line is selected from a list of design lines consisting of: (i) a linear path, (ii) a circular path, and (iii) a path having a bifurcation shape.

3. The method according to claim 1, wherein receiving the design line comprises receiving a planning of one or more ablation lines for ablating tissue on the first surface of the organ.

4. The method according to claim 1, wherein the organ comprises a heart, and wherein selecting the properties comprise selecting at list one of the one or more properties from a list of properties consisting of: (i) a local activation time of a wave propagating in the heart, (ii) a local direction of the wave propagating in the heart, (iii) a fractionated electrical signal, (iv) a conduction speed of the wave propagating in the heart, (v) an electrical parameter of an electrical signal in the heart, (vi) a scar in tissue of the heart, and (vii) an intersection of waves propagating in the heart.

5. The method according to claim 1, wherein visualizing the properties comprises applying, to the design line, one or more types of annotations indicative of a respective property of the one or more properties.

6. The method according to claim 5, wherein at least one of the annotations is selected from a list of annotations consisting of: (i) a jagged section of the design line, (ii) an altering thickness of a first respective section of the design line, (iii) an altering color of a second respective section of the design line, (iv) a geometric shape marked on a third respective section of the design line, and (v) first and second geometrical shapes placed, respectively, at first and second locations on the design line, so as to form a given section having the respective property.

7. The method according to claim 6, wherein at least one of the altering thickness and altering color is indicative of a magnitude of the respective property.

8. The method according to claim 6, wherein the first and second geometrical shapes comprise first and second lines orthogonal to the design line, and wherein the respective property comprises a scar contained within the given section.

9. The method according to claim 1, further comprising, in response to visualizing the one or more properties falling along the design line, adjusting at least one of: (i) a path of the received design line, and (ii) the selection of at least one of the properties.

10. A system for displaying annotations on a design line provided on the surface of an anatomical map, comprising:
   a processor, which is configured to:
      receive an anatomical map of a patient organ, the anatomical map comprising properties obtained at respective locations on a first surface of the organ;
      receive a design line produced on a second surface of the anatomical map, wherein the second surface models the first surface in the anatomical map; and
      select, or receive a selection of, one or more of the properties that, when falling along the design line, will be visualized thereon; and
   an output device, which is configured to visualize the one or more properties falling along the design line.

11. The system according to claim 10, wherein the received design line is selected from a list of design lines consisting of: (i) a linear path, (ii) a circular path, and (iii) a path having a bifurcation shape.

12. The system according to claim 10, wherein the received design line comprises a planning of one or more ablation lines for ablating tissue on the first surface of the organ.

13. The system according to claim 10, wherein the organ comprises a heart, and wherein the processor is configured to select, or to receive a selection of, at list one of the one or more properties from a list of properties consisting of: (i) a local activation time of a wave propagating in the heart, (ii) a local direction of the wave propagating in the heart, (iii) a fractionated electrical signal, (iv) a conduction speed of the wave propagating in the heart, (v) an electrical parameter of an electrical signal in the heart, (vi) a scar in tissue of the heart, and (vii) an intersection of waves propagating in the heart.

14. The system according to claim 10, wherein the processor is configured to apply, to the design line, one or more types of annotations indicative of a respective property of the one or more properties, and wherein the output device is configured to display the one or more types of annotations overlaid on the design line.

15. The system according to claim 14, wherein at least one of the annotations is selected from a list of annotations consisting of: (i) a jagged section of the design line, (ii) an altering thickness of a first respective section of the design line, (iii) an altering color of a second respective section of the design line, (iv) a geometric shape marked on a third respective section of the design line, and (v) first and second geometrical shapes placed, respectively, at first and second locations on the design line, so as to form a given section having the respective property.

16. The system according to claim 15, wherein at least one of the altering thickness and altering color is indicative of a magnitude of the respective property.

17. The system according to claim 15, wherein the first and second geometrical shapes comprise first and second lines orthogonal to the design line, and wherein the respective property comprises a scar contained within the given section.

18. The system according to claim 10, further comprising, in response to visualizing the one or more properties falling along the design line, the processor is configured to receive or produce at least one of: (i) an adjusted path of the received design line, and (ii) an adjusted selection of at least one of the properties.

19. The method according to claim 1, wherein the design line comprises areas of tissue planned for ablation.

20. The system according to claim 10, wherein the design line comprises areas of tissue planned for ablation.

\* \* \* \* \*